(12) United States Patent
de la Rama et al.

(10) Patent No.: US 7,285,116 B2
(45) Date of Patent: Oct. 23, 2007

(54) NON-CONTACT TISSUE ABLATION DEVICE AND METHODS THEREOF

(75) Inventors: Alan de la Rama, Cerritos, CA (US); Tho Hoang Nguyen, Huntington Beach, CA (US); Vivian Tran, Santa Ana, CA (US); Cary K. Hata, Tustin, CA (US); Peter C Chen, Irvine, CA (US)

(73) Assignee: Irvine Biomedical Inc., Irvine, CA (US)

( * ) Notice: Subject to any disclaimer, the term of this patent is extended or adjusted under 35 U.S.C. 154(b) by 124 days.

(21) Appl. No.: 10/845,798

(22) Filed: May 15, 2004

(65) Prior Publication Data

US 2005/0256518 A1  Nov. 17, 2005

(51) Int. Cl.
*A61B 18/14* (2006.01)

(52) U.S. Cl. ............ 606/27; 606/28; 606/32; 606/41; 600/439; 600/459; 600/466

(58) Field of Classification Search ........ 600/439, 600/459, 466; 606/27, 28, 41, 32, 48–50
See application file for complete search history.

(56) References Cited

U.S. PATENT DOCUMENTS

| | | | |
|---|---|---|---|
| 5,295,484 A * | 3/1994 | Marcus et al. ........... 600/439 |
| 5,545,161 A * | 8/1996 | Imran ...................... 606/41 |
| 5,620,479 A * | 4/1997 | Diederich ................ 601/3 |
| 5,676,693 A | 10/1997 | LaFontaine | |
| 5,697,927 A | 12/1997 | Imran et al. | |
| 5,735,811 A * | 4/1998 | Brisken ..................... 604/22 |
| 5,846,218 A * | 12/1998 | Brisken et al. ............ 604/22 |
| 5,921,982 A * | 7/1999 | Lesh et al. ................ 606/41 |
| 5,971,980 A * | 10/1999 | Sherman .................. 606/34 |
| 5,971,983 A * | 10/1999 | Lesh ......................... 606/41 |
| 5,997,532 A | 12/1999 | McLaughlin et al. | |
| 6,004,269 A * | 12/1999 | Crowley et al. ........... 600/439 |
| 6,007,530 A * | 12/1999 | Dornhofer et al. ........ 606/1 |
| 6,012,457 A | 1/2000 | Lesh | |
| 6,083,170 A * | 7/2000 | Ben-Haim ................. 600/463 |
| 6,120,476 A | 9/2000 | Fung et al. | |
| 6,161,543 A * | 12/2000 | Cox et al. ................. 128/898 |
| 6,164,283 A | 12/2000 | Lesh | |
| 6,206,831 B1 * | 3/2001 | Suorsa et al. ............. 600/439 |
| 6,206,842 B1 * | 3/2001 | Tu et al. ................... 601/2 |
| 6,241,666 B1 * | 6/2001 | Pomeranz et al. ........ 600/381 |
| 6,241,727 B1 | 6/2001 | Tu | |
| 6,245,064 B1 | 6/2001 | Lesh et al. | |
| 6,264,654 B1 | 7/2001 | Swartz et al. | |
| 6,315,777 B1 | 11/2001 | Comben | |

(Continued)

FOREIGN PATENT DOCUMENTS

WO   WO96/29935   10/1996

*Primary Examiner*—Michael Peffley
*Assistant Examiner*—Alex Toy
(74) *Attorney, Agent, or Firm*—Raymond Sun (57) ABSTRACT

A catheter for ablating body tissue of the interior regions of the heart includes a handle assembly, a shaft, and a distal tip section coupled to the distal end of the shaft. The distal tip section has a non-compliant and non-porous cap that has a tubular wall that defines a bore, and an ablation element that is housed inside the bore and spaced apart from the wall of the cap.

17 Claims, 6 Drawing Sheets

U.S. PATENT DOCUMENTS

| | | |
|---|---|---|
| 6,524,251 B2 | 2/2003 | Rabiner et al. |
| 6,579,288 B1 | 6/2003 | Swanson et al. |
| 6,602,242 B1 | 8/2003 | Fung et al. |
| 6,671,533 B2 | 12/2003 | Chen et al. |
| 6,672,312 B2 * | 1/2004 | Acker ........................ 128/898 |
| 2002/0115990 A1 * | 8/2002 | Acker .......................... 606/27 |
| 2004/0049148 A1 * | 3/2004 | Rodriguez et al. ............ 604/22 |
| 2004/0077976 A1 | 4/2004 | Wilson |
| 2005/0197577 A1 * | 9/2005 | Makin et al. ................ 600/439 |

* cited by examiner

SECTION A-A

FIG. 5

SECTION B-B

FIG. 6

NON-CONTACT TISSUE ABLATION DEVICE AND METHODS THEREOF

BACKGROUND OF THE INVENTION

1. Field of the Invention

The present invention is directed to systems and methods for mapping and ablating body tissue of the interior regions of the heart. More particularly, this invention relates to catheters and methods for ablating cardiac tissues using a deflectable catheter having an irrigated ablation element for the treatment of cardiac arrhythmia, for example atrial fibrillation and ventricular tachycardia.

2. Description of the Prior Art

Abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the endocardial surface of the chambers of the heart. The heart includes a number of normal pathways which are responsible for the propagation of electrical signals from the upper to the lower chambers necessary for performing normal systole and diastole function. The presence of an arrhythmogenic site or an accessory pathway can bypass or short circuit the normal pathway, potentially resulting in very rapid heart contractions or tachycardias.

Treatment of tachycardias may be accomplished by a variety of approaches, including medications, implantable pacemakers/defibrillators, surgery and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by blocking or ablating the abnormal arrhythmogenic tissue or accessory pathway responsible for the tachycardia.

Of particular interest to the present invention is radiofrequency (RF) ablation technique which has been proven to be highly effective in tachycardia treatment while exposing a patient to minimal side effects and risks. RF catheter ablation is generally performed after conducting an initial mapping study where the locations of the arrhythmogenic site and/or accessory pathway are determined by diagnostic electrophysiology catheters which are connected to commercially available EP monitoring systems. After a mapping study, an ablation catheter is usually introduced to the target region inside the heart and is manipulated so that the ablation tip electrode lies exactly at the target tissue site. RF energy or other suitable energy is then applied through the tip electrode to the cardiac tissue in order to ablate the tissue of the arrhythmogenic site or the accessory pathway. By successfully destroying that tissue, the abnormal signal patterns responsible for the tachycardia may be eliminated.

Atrial fibrillation (AF) is one type of cardiac arrhythmia believed to be the result of the simultaneous occurrence of multiple wavelets of functional re-entry of electrical impulses within the atria, resulting in a condition in which the transmission of electrical activity becomes so disorganized that the atria contracts irregularly. AF is a common arrhythmia associated with significant morbidity and mortality. A number of clinical conditions may arise from irregular cardiac functions and the resulting hemodynamic abnormalities associated with AF, including stroke, heart failure and other thromboembolic events. AF is a significant cause of cerebral stroke, wherein the fibrillating motion in the left atrium induces the formation of thrombus. A thromboembolism is subsequently dislodged into the left ventricle and enters the cerebral circulation where stroke may occur.

For many years, the only curative treatment for AF has been surgical, with extensive atrial incisions used to compartmentalize the atrial mass from the other cardiac tissue. The surgical "maze" procedure, as it is commonly known, includes, in the left atrium creating vertical incisions from the superior pulmonary veins, to the inferior pulmonary veins and ending in the mitral valve annulus, with an additional horizontal incision linking the upper ends of the vertical lines. It is believed that ectopic beats originating within or at the ostium of the pulmonary veins (PV) may be the source of paroxysmal and even persistent AF. As a result, a series of multiple point RF ablations to create linear patterns in the left atrium has been used to replicate surgical procedures in patients with paroxysmal or chronic AF. Although successful, there are instances in which this technique may leave gaps between lesions giving opportunities for reentrant circuits to reappear. Another challenge with using this approach is the high incidence of pulmonary vein (PV) stenosis.

Different energy sources have been utilized for electrically isolating the pulmonary veins from the atrium. These include RF, laser, microwave, cryoablation, light, and ultrasound energy. Each energy source has its advantages and disadvantages and PV isolation has been achieved to different degrees of success. Moreover several researchers have recently suggested that catheter ablation using ultrasound energy may reduce the incidence of PV stenosis.

Ventricular tachycardia (VT) is another abnormal heart rhythm that can be treated by catheter-based mapping and ablation systems. VT is an arrhythmia that results from electrical impulses arising from the ventricles instead of the heart's natural pacemaker known as the sinoatrial (SA) node. Due to the fact that electrical impulses are not conducting from the SA node to the ventricles, the ventricles contract abnormally very rapidly. As a result, the four chambers of the heart are less able to fill completely with blood between beats, and hence less blood is pumped to the remaining circulatory pathways in the body. Over time, VT can lead to heart failure or degenerate into ventricular fibrillation, which can result in myocardial infarction. The most common treatment for VT is antiarrhythmic medication, however if drugs are not effective, cardioversion may be recommended. Patients who still suffer from episodes of VT may require an implantable cardioverter defibrillator. Although RF catheter ablation as a treatment for VT has been performed, success has been limited particularly to those VT's due to ischemic heart disease. This may be due to the difficulty in achieving sufficient tissue penetration of RF energy to ablate arrhythmia circuit lying beneath the endocardial scar tissue. In addition, the ventricles are naturally much thicker than atrial tissues and creating transmural lesions is more challenging when utilizing conventional RF ablation techniques. Irrigated tip RF ablation catheters have recently been introduced to create deeper and larger lesions and have achieved the transmurality of the cardiac wall, however further improvements in performance is desirable. This may be due to the irregular endocardial surface of the ventricular trabeculum that may present a technical challenge for ablating electrodes of RF ablation catheters to make adequate tissue contact.

Cardiac ablation with ultrasound energy however, does not require good contact with the underlying tissue. Ultrasound energy propagates as a mechanical wave within the surrounding medium, and in the tissue the vibrating motion is converted into heat. Therefore the tissue does not need to be in intimate contact with the ultrasound transducer unlike in the case of RF ablating electrodes. At a designated zone within the tissue, the tissue at the target area can be heated to a sufficiently high temperature for ablation, while tissue surrounding the target area is subject to a lower intensity ultrasound energy and not damaged.

In order to produce thermal effect in the tissue, the ultrasound emitting member has a transducer. The piezoelectric nature of ultrasound transducers creates limitations for these materials. One major limitation is when the temperature of the transducer is elevated, the performance decreases steadily until no acoustic waves can be observed. One way to keep the operating temperature of this material cool is to irrigate the transducer. A cooling medium such as water is introduced or pumped through the catheter in order to dissipate heat in the housing and effect cooling of the transducer, including cooling of the external tissue surface to avoid unwanted tissue damage. Schaer et al in U.S. Pat. No. 6,522,930 describes a tissue ablation device in which the ablation element is covered by a tubular porous membrane that allows pressurized fluid to pass therethrough for ablatively coupling the ablation element to a tissue site. McLaughlin et al in U.S. Pat. No. 5,997,532 also describes an ablation catheter having a porous, non-conductive buffer layer over the tip electrode. In both the Schaer et al. and McLaughlin et al. catheters, the amount of irrigation fluid permeating out from the porous membrane or porous tip electrode to cool the tissue-ablation element interface may not be consistent due to its contact with the underlying tissue and therefore may produce a larger or smaller intended ablation area. This phenomenon can be more pronounced in irregular endocardial surfaces such as the ventricular trabeculae.

Thus, there still remains a need for a catheter-based system and method that provides improved ablation performance at the treatment location, especially in irregular endocardial surfaces.

SUMMARY OF THE DISCLOSURE

It is an objective of the present invention to provide a system and method that accurately positions a catheter at the desired treatment location.

It is another objective of the present invention to provide a system and method that provides improved ablation performance at the treatment location, especially in irregular endocardial surfaces.

In order to accomplish the objects of the present invention, there is provided a catheter for ablating body tissue of the interior regions of the heart. The catheter includes a handle assembly, a shaft, and a distal tip section coupled to the distal end of the shaft. The distal tip section has a non-compliant and non-porous cap that has a tubular wall that defines a bore, and an ablation element that is housed inside the bore and spaced apart from the wall of the cap.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides a catheter for ablating body tissue of the interior regions of the heart. The catheter includes a handle assembly, a shaft, and a distal tip section coupled to the distal end of the shaft. The distal tip section has a non-compliant and non-porous cap that has a tubular wall that defines a bore, and an ablation element that is housed inside the bore and spaced apart from the wall of the cap.

Even though the present invention will be described hereinafter in connection with treating AF or VT, it is understood that the principles of the present invention are not so limited, but can be used in other applications (e.g., treatment of accessory pathways, atrial flutter), and in other body pathways (e.g., right atrium, left atrium, superior vena cava, right ventricle, left ventricle, pulmonary veins).

FIGS. 1-6 illustrate a catheter system 20 according to one embodiment of the present invention. The catheter system 20 has a tubular shaft 22 having a distal end 26, a proximal end 28, and a main lumen 30 extending through the shaft 22. A distal tip section 24 is secured to the distal end 26 of the shaft 22. A handle assembly 32 is attached to the proximal end 28 of the shaft 22 using techniques that are well-known in the catheter art.

Figure 3:
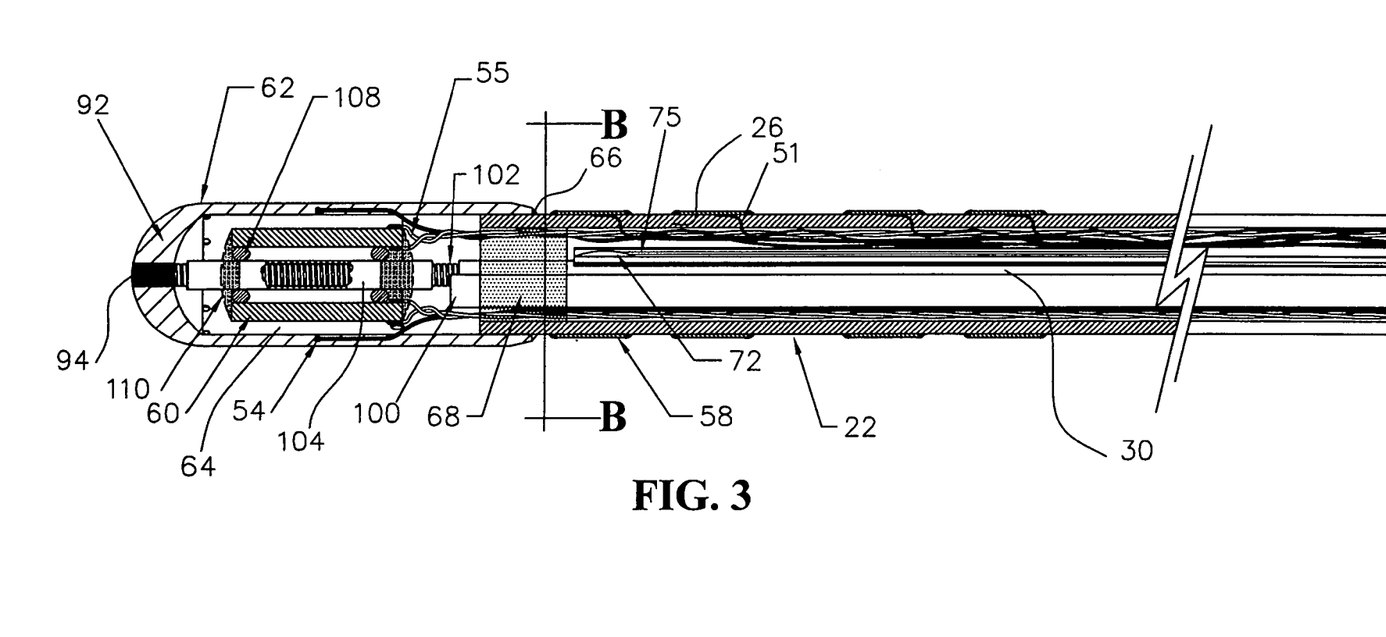
FIG. 3 is an enlarged cross-sectional view of the distal tip section of the catheter of FIGS. 1 and 2.

The distal tip section 24 has an ablation element 60 that is housed inside a non-compliant and non-porous tubular cap 62. The ablation element 60 is spaced from, and does not contact, the walls of the cap 62. The cap 62 has a bore 64 extending therethrough. The distal end 26 of the shaft 22 is slide-fitted into the bore 64 at the proximal end 66 of the cap 62, and secured to the cap 62 by adhesive bonding. An inner sleeve 68 is secured by adhesive bonding in the main lumen 30 at the distal end 26 of the shaft 22. The inner sleeve 68 is made of a plastic material such as PEEK and has multiple channels 67 (see FIG. 6) separating the wires, an inner supporting member 102, and a fluid lumen so they do not interfere with each other inside the cap 62 when the catheter is subjected to mechanical forces during use, including deflection of the distal tip, torque, and advancement and withdrawal from the patient. The cap 62 can be made from a non-compliant material such as polyethylene, polyurethane, polyolefins, polymethylpentene, and the like, that is capable of allowing ultrasound energy to be transmitted therethrough. The cap 62 extends from its proximal end 66 and terminates at a closed distal tip 92 that has an opening 94 provided thereat.

The ablation element 60 can be embodied in the form of a transducer or an electrode that includes a piezoelectric crystal which converts electrical energy into ultrasound energy. The transducer 60 is tubular, and O-rings 108 are positioned between the transducer 60 and a tubular outer supporting member 104 to create an air space between the supporting member 104 and the transducer 60 to minimize transmission of ultrasound waves inside the transducer 60. A silicone adhesive 110 seals the ends of the transducer 60. Irrigation fluid fills the space between the transducer 60 and the cap 62, so that the ultrasound energy can be transmitted through the fluid and the cap 62 into the body tissue. The fluid acts to cool the transducer 60, and functions as a medium to transmit the ultrasound energy. Since the transducer 60 has a diameter that is smaller than the inner diameter of the cap 62, the transducer 60 does not contact the body tissue.

An irrigation tube 100 extends through the main lumen 30 of the shaft 22, and has a distal end that terminates inside the proximal end 66 of the cap 62, at a location proximal to the transducer 60. Irrigation fluid is introduced from a pump 120 via a standard infusion tube 35 and a luer fitting 34 through the irrigation tube 100 to be delivered inside the bore 64 of the cap 62 for cooling the transducer 60.

The inner supporting member 102 extends through the main lumen 30 of the shaft 22 and the bore 64 of the cap 62, terminating adjacent the opening 94 in the distal tip 92. The inner supporting member 102 functions to provide support to the catheter shaft 22 and the distal tip section 24, and is received inside the outer supporting member 104 that extends through the inner sleeve 68 and into the bore 64. The inner supporting member 102 can be provided in the form of a coil, a flat wire, or a rod composed of metal, alloy or a polymer.

A plurality of thermocouple wires 54 can have their distal tips secured to the inner surface of the cap 62, and are used to detect the temperature at the ablation site.

Figure 4:
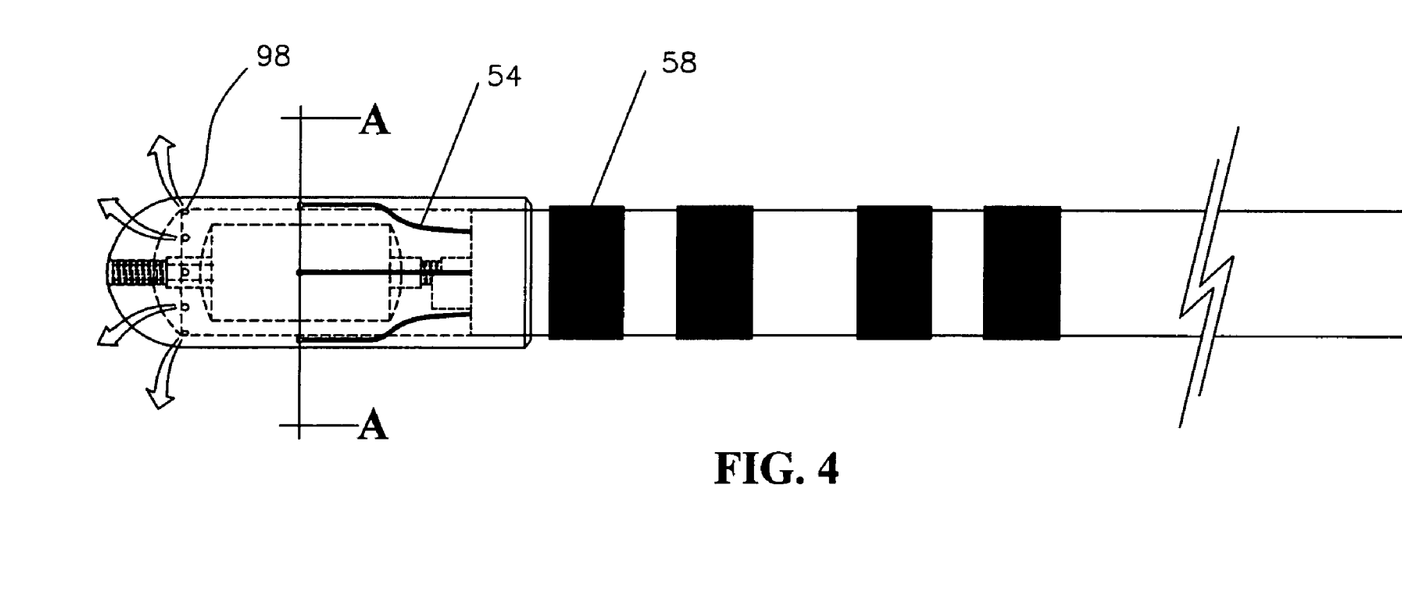
FIG. 4 is an enlarged side plan view of the distal tip section of the catheter of FIGS. 1 and 2.
Figure 5:
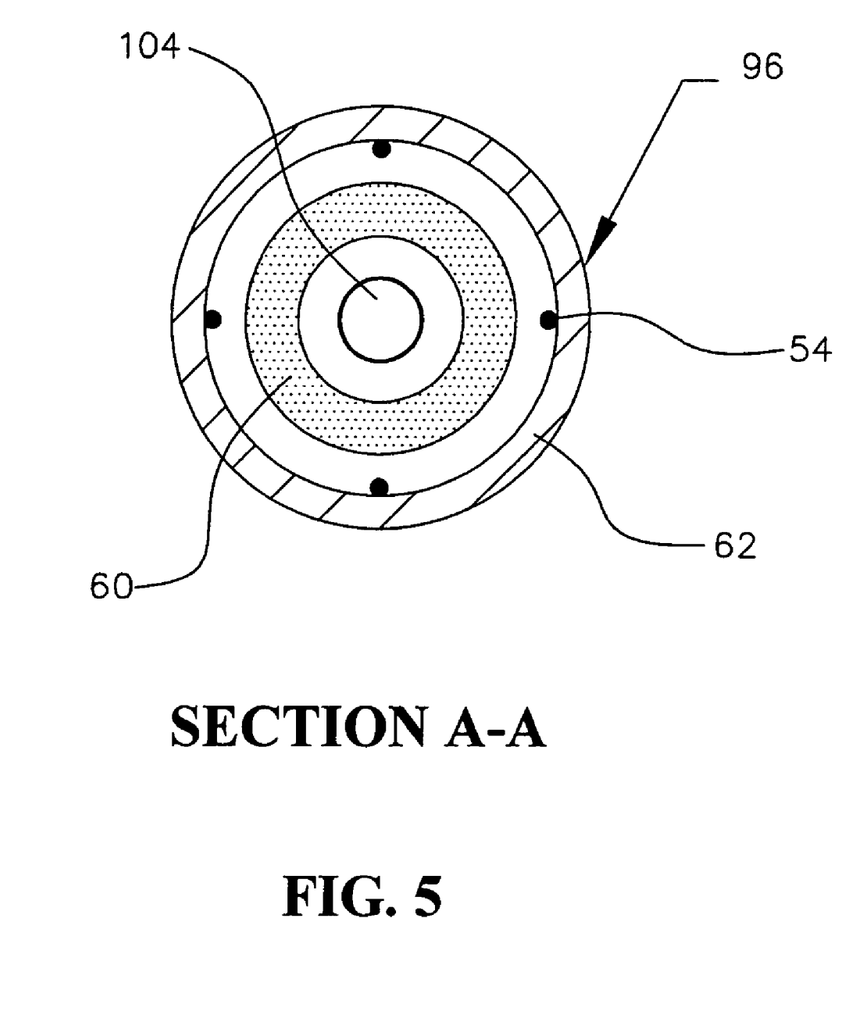
FIG. 5 is a cross-sectional view of the distal tip section of FIG. 4 taken along lines A-A thereof.
Figure 6:
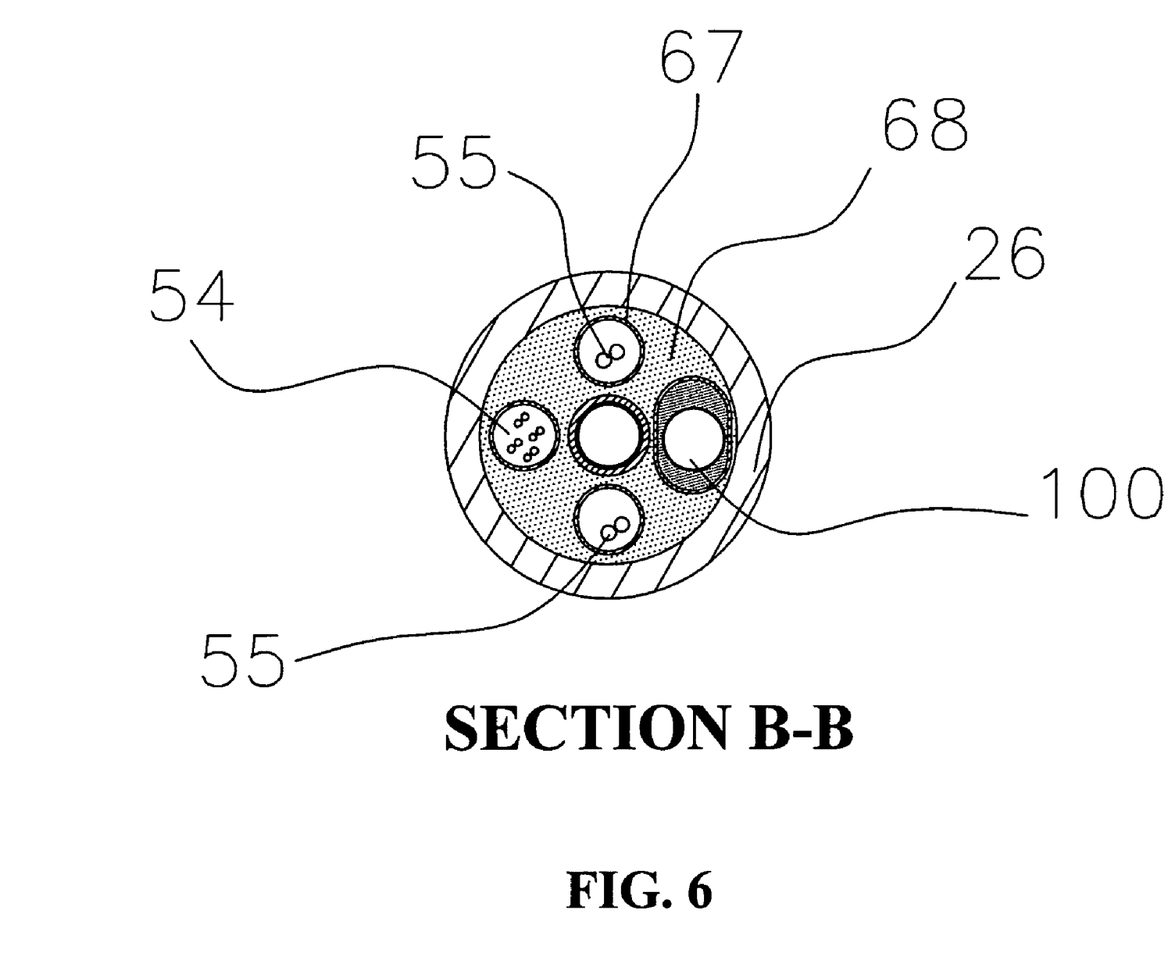
FIG. 6 is a cross-sectional view of the distal tip section of FIG. 3 taken along lines B-B thereof.

A plurality of ring electrodes 58 are provided in spaced-apart manner about the outer surface of the shaft 22 adjacent the distal tip section 24. The ring electrodes 58 can be made of a solid, electrically conducting material, like platinum-iridium, stainless steel, or gold, that is attached about the shaft 22. Alternatively, the ring electrodes 58 can be formed by coating the exterior surface of the shaft 22 with an electrically conducting material, such as platinum-iridium or gold. The coating can be applied by sputtering, ion beam deposition or similar known techniques. The number of ring electrodes 58 can vary depending on the particular geometry of the region of use and the functionality desired.

Figure 1:
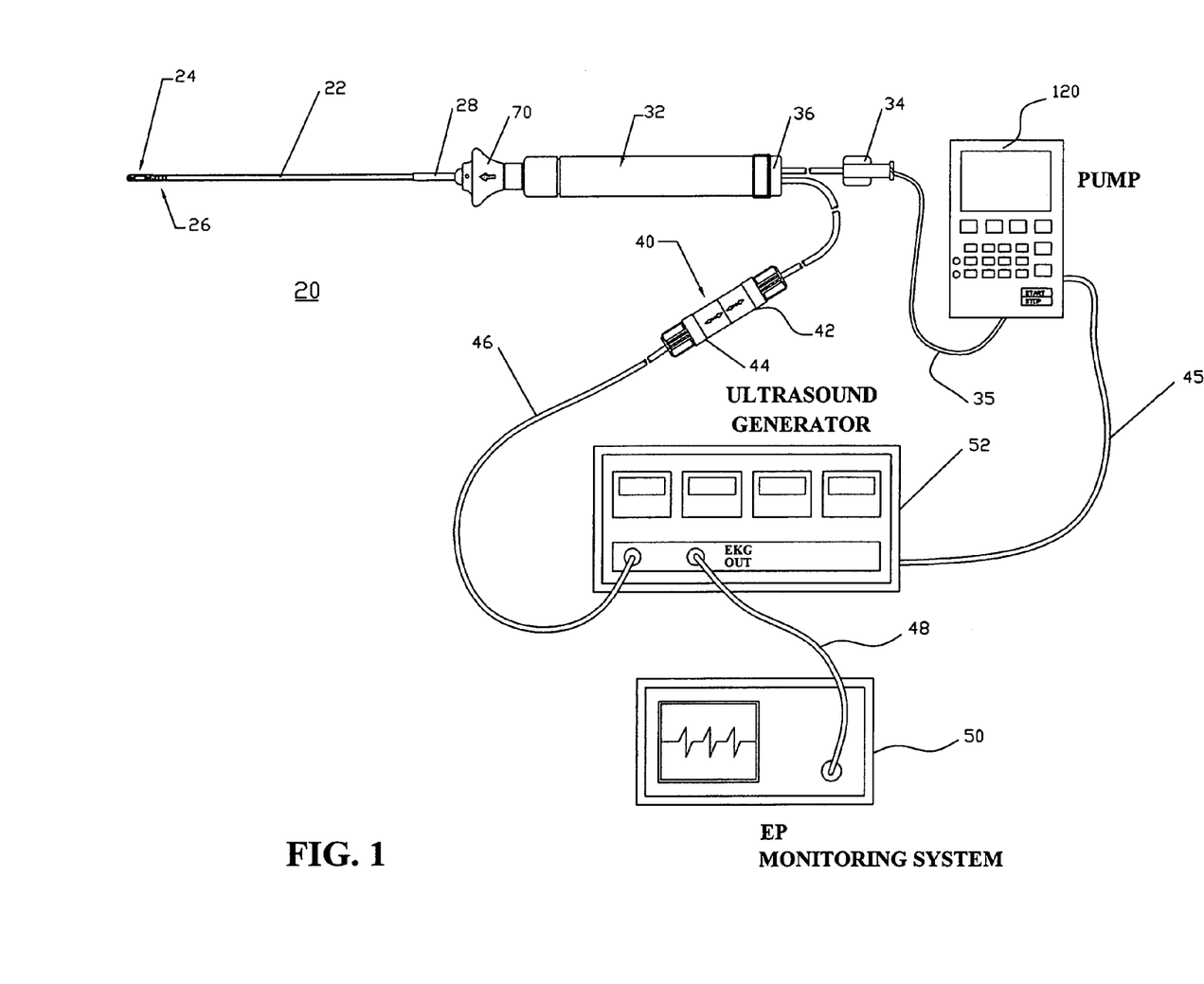
FIG. 1 illustrates a mapping and ablation system according to one embodiment of the present invention.

As will be explained in greater detail below, the ring electrodes 58 function to map the region of the heart that is to be treated. After the mapping has been completed, the transducer 60 is positioned at the location where ablation is to be performed, and the irrigation fluid through the lumen tube 100 is increased to the desired flow rate set on the pump 120. The flow of the irrigation fluid is software-controlled and its instructions are transmitted from the generator 52 to the pump 120 through the cable 45. The ablation is then carried out by energy that is emitted from the transducer 60 through the irrigation media (e.g., fluid, saline, contrast media or mixture) inside the cap 62.

Figure 2:
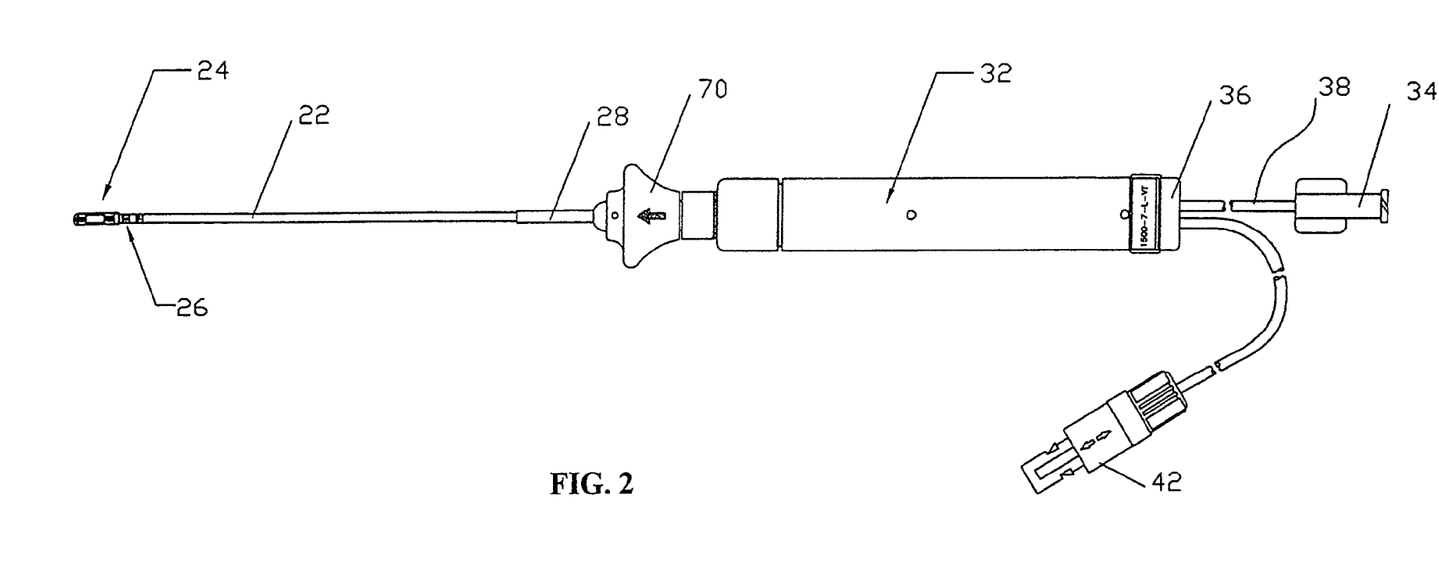
FIG. 2 is a side plan view of the catheter of the system of FIG. 1.

A standard luer fitting 34 is connected to the proximal end of the tubing 38 extending out from the proximal end 36 of the handle assembly 32 using techniques that are well-known in the catheter art. The luer fitting 34 provides a fluid line for irrigation media to be introduced to cool the transducer 60 at the distal tip section 24 of the shaft 22. The irrigation media is delivered via the infusion tube 35 and into the irrigation tube 100 that extends from the luer fitting 34, and terminates in the bore 64 of the cap 62. The irrigation media exits from the holes 98 located distally of the transducer 60 at the distal end of the cap 62. In another embodiment, the cap 62 is completely closed without the distally located holes 98, and the irrigation media entering the bore 64 is withdrawn back out through another lumen tube (not shown) towards the proximal end of the catheter.

A connector assembly 40 is also connected to the proximal end 36 of the handle assembly 32 using techniques that are well-known in the catheter art. The connector assembly 40 has a proximal connector 42 that couples the handle assembly 32 to the connector 44 of a cable 46 that leads to an ultrasound generator 52. An EP monitoring system 50 is coupled to the ultrasound generator 52 via another cable 48. The EP monitoring system 50 can be a conventional EP monitor which receives (via the ultrasound generator 52) electrical signals detected by the electrodes 58, and processes and displays these intracardiac signals to assist the physician in locating the arrhythmogenic sites or pathways. The ultrasound generator 52 can be a conventional ultrasound generator that creates and transmits ablating energy to the transducer 60, which emits the acoustic energy to ablate the tissue that extends radially from the position of the cap 62.

Conductor wires 51 extend from the ultrasound generator 52 along the cables 46 and 48 (through the connector assembly 40, the handle assembly 32 and the lumen 30 of the shaft 22) to the distal tip section 24, where the conductor wires 51 couple the ring electrodes 58. The thermocouple wires 54 couple the cap 62, and the ultrasound wires 55 couple the transducer 60. The thermocouple wires 54 and ultrasound wires 55 can extend from the cap 62 and transducer 60 through the channels 67 of the inner sleeve 68 and through the lumen 30 of the shaft 22 and the handle assembly 32 to the proximal connector 42, where they can be electrically coupled by the internal thermocouple wires in the cable 46 to the ultrasound generator 52 where the temperature can be displayed.

The handle assembly 32 also includes a steering mechanism 70 that functions to deflect the distal tip section 24 of the shaft 22 for maneuvering and positioning the distal tip section 24 at the desired location in the heart. Referring to FIG. 3, the steering mechanism 70 includes a steering wire 72 that extends in the main lumen 30 of the shaft 22 from its proximal end at the handle assembly 32 to its distal end which terminates at the distal end 26 of the shaft 22 before the location of the distal tip section 24. The distal end of the steering wire 72 is secured to a flat wire 75 that is fixedly positioned inside the handle assembly 32. The flat wire 75 extends in the lumen 30 from the anchor to its distal end at a location slightly proximal to the inner sleeve 68. The flat wire 75 is attached to the steering wire 72 at the distal ends of the flat wire 75 and the steering wire 72 so as to be controlled by the steering wire 72. Specifically, by pushing the steering mechanism 70 forward in a distal direction, the steering mechanism 70 will pull the steering wire 72 in a proximal direction, causing the distal tip section 24 to deflect to one direction. By pulling back the steering mechanism 70 in a proximal direction, the steering wire 72 is deactivated and the distal tip section 24 returns to its neutral position or deflects to the opposite direction for bi-directionality.

The operation and use of the catheter system 20 will now be described. To introduce and deploy the distal tip section 24 within the heart, the physician uses a conventional introducer sheath to establish access to a selected artery or vein. The physician introduces the shaft 22 through a conventional hemostasis valve on the introducer and progressively advances the catheter through the access vein or artery into the desired location within the heart. The physician observes the progress of the catheter using fluoroscopic or ultrasound imaging. The catheter can include a radio-opaque compound, such as barium sulfate, for this purpose. Alternatively, radio-opaque markers can be placed at the distal end of the introducer sheath.

The shaft 22 and the introducer sheath can be maneuvered to the right atrium by the steering mechanism 70. Once located in the right atrium or ventricle, good contact is established when the ring electrodes 58 contact the target endocardial tissue, and the intracardiac signals of the selected region are recorded through the ring electrodes 58. The results of the mapping operation are processed and displayed at the EP monitoring system 50. A differential input amplifier (not shown) in the EP monitoring system 50 processes the electrical signals received from the ring electrodes 58 via the wires 51, and converts them to graphic images that can be displayed. The thermocouple wires 54 can also function to monitor the temperature of the surrounding tissue, and provide temperature information to the ultrasound generator 52.

Once the desired position of the transducer 60 has been confirmed by mapping through the ring electrodes 58, and visually through fluoroscopy, the physician can then increase the irrigation fluid flow rate by turning the power of the ultrasound generator 52 on which controls the fluid flow rate prior to the start of ablation. The ultrasound generator 52 delivers high frequency energy that is propagated through the wires 55 to the ultrasound transducer 60 that is positioned inside the cap 62. The acoustic energy radiates in a radial manner from the transducer 60, propagates through the irrigation media (which acts as an energy transmitting medium), exits the cap 62 and then reaches the selected tissue (typically in a pressure waveform) to ablate the tissue.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A catheter for ablating body tissue of the interior regions of the heart, comprising:
   a handle assembly;
   a shaft having a main lumen, a proximal end coupled to the handle assembly, and a distal end;
   a distal tip section coupled to the distal end of the shaft, the distal tip section having:
      a non-compliant and non-porous cap that has a tubular wall that defines a bore; and
      an ablation element that is housed inside the bore and spaced apart from the wall of the cap, the ablation element producing acoustic energy; and
   an irrigation tube extending through the main lumen and having a distal end that terminates in the bore.

2. The catheter of claim 1, wherein the ablation element is a transducer.

3. The catheter of claim 1, further including irrigation fluid in the bore between the tubular wall and the ablation element.

4. The catheter of claim 1, further including a plurality of ring electrodes provided in a spaced-apart manner about the outer surface of the shaft adjacent the distal tip section.

5. The catheter of claim 1, further including an inner sleeve secured in the main lumen at the distal end of the shaft.

6. The catheter of claim 1, further including an inner supporting member that extends through the main lumen of the shaft and the bore of the cap.

7. The catheter of claim 6, wherein the inner supporting member is provided in the form of a coil, a flat wire, or a rod composed of metal, alloy or a polymer.

8. The catheter of claim 1, further including a plurality of thermocouple wires that are connected to the cap.

9. The catheter of claim 1, further including a steering mechanism that extends in the main lumen of the shaft and which terminates at the distal end of the shaft before the location of the distal tip section.

10. A catheter for ablating body tissue of the interior regions of the heart, comprising:
    a handle assembly;
    a shaft having a main lumen, a proximal end coupled to the handle assembly, and a distal end;
    an inner sleeve secured in the main lumen;
    a distal tip section coupled to the distal end of the shaft, the distal tip section having:
       a non-compliant and non-porous cap that has a tubular wall that defines a bore; and
       an ablation element that is housed inside the bore and spaced apart from the wall of the cap, the ablation element producing acoustic energy
    an inner supporting member that extends through the main lumen of the shaft and the bore of the cap; and
    an outer supporting member that extends through the inner sleeve and into the bore, with the inner supporting member housed in the outer supporting member.

11. The catheter of claim 10, wherein the ablation element is a transducer.

12. The catheter of claim 10, further including irrigation fluid in the bore between the tubular wall and the ablation element.

13. The catheter of claim 10, further including a plurality of ring electrodes provided in a spaced-apart manner about the outer surface of the shaft adjacent the distal tip section.

14. The catheter of claim 10, wherein the inner sleeve is secured in the main lumen at the distal end of the shaft.

15. The catheter of claim 10, wherein the inner supporting member is provided in the form of a coil, a flat wire, or a rod composed of metal, alloy or a polymer.

16. The catheter of claim 10, further including a plurality of thermocouple wires that are connected to the cap.

17. The catheter of claim 10, further including a steering mechanism that extends in the main lumen of the shaft and which terminates at the distal end of the shaft before the location of the distal tip section.

* * * * *